United States Patent
Yoshimasa et al.

(10) Patent No.: US 6,858,771 B2
(45) Date of Patent: Feb. 22, 2005

(54) ABSORBENT ARTICLE WITH COMPRESSED GROOVES

(75) Inventors: Wataru Yoshimasa, Kagawa (JP); Kazuya Nishitani, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 292 days.

(21) Appl. No.: 10/187,816

(22) Filed: Jul. 3, 2002

(65) Prior Publication Data

US 2003/0088231 A1 May 8, 2003

(30) Foreign Application Priority Data

Jul. 12, 2001 (JP) ........................................ 2001-212898

(51) Int. Cl.[7] .............................................. A61F 13/15
(52) U.S. Cl. ................ 604/380; 604/385.101
(58) Field of Search ............................... 604/378–380, 604/385.01, 385.23, 385.101

(56) References Cited

U.S. PATENT DOCUMENTS

| | | | | | |
|---|---|---|---|---|---|
| 5,451,442 | A | * | 9/1995 | Pieniak et al. ................. | 428/54 |
| 5,591,149 | A | * | 1/1997 | Cree et al. .................... | 604/378 |
| 5,681,300 | A | | 10/1997 | Ahr et al. | |
| 5,891,118 | A | * | 4/1999 | Toyoshima et al. ......... | 604/366 |
| 6,410,822 | B1 | * | 6/2002 | Mizutani ...................... | 604/380 |
| 6,517,525 | B1 | * | 2/2003 | Berthou et al. ........ | 604/385.101 |
| 6,558,363 | B2 | * | 5/2003 | Keuhn et al. .......... | 604/385.01 |
| 6,679,104 | B2 | * | 1/2004 | Sorebo .......................... | 73/73 |
| 6,689,113 | B2 | * | 2/2004 | Boulanger et al. ..... | 604/385.04 |
| 2001/0027305 | A1 | * | 10/2001 | Raidel et al. .......... | 604/385.101 |
| 2001/0039405 | A1 | * | 11/2001 | Keuhn et al. ............... | 604/360 |
| 2001/0044610 | A1 | * | 11/2001 | Kim et al. ................... | 604/365 |
| 2003/0018314 | A1 | * | 1/2003 | Nozaki et al. .......... | 604/385.101 |
| 2003/0088222 | A1 | * | 5/2003 | Yoshimasa et al. .......... | 604/380 |
| 2003/0135182 | A1 | * | 7/2003 | Woon et al. ................. | 604/378 |

FOREIGN PATENT DOCUMENTS

| | | | |
|---|---|---|---|
| EP | 0 948 951 A2 | 10/1999 | |
| JP | 7-500759 | 1/1995 | ........... A61F/13/15 |
| WO | 93/09745 | 5/1993 | ........... A61F/13/46 |
| WO | WO-99/05999 A1 | 2/1999 | |

* cited by examiner

Primary Examiner—Larry I. Schwartz
Assistant Examiner—Michael G. Bogart
(74) Attorney, Agent, or Firm—Darby & Darby

(57) ABSTRACT

Disclosed is an absorbent article including a backsheet, an absorbent storage layer, a liquid guide layer, and a top layer. The absorbent storage layer, the liquid guide layer and the top layer satisfy the following relationships: the liquid guide layer>the absorbent storage layer>the top layer with respect to a water absorbency due to capillary phenomenon; the liquid guide layer>the absorbent storage layer>the top layer with respect to a retention ratio of a liquid dropped onto the top layer in an amount less than a maximum water absorption amount of the liquid guide layer; and the absorbent storage layer>the liquid guide layer>the top layer with respect to a retention ratio of a liquid dropped onto the top layer in an amount more than the maximum water absorption amount of the liquid guide layer.

7 Claims, 3 Drawing Sheets

ABSORBENT ARTICLE WITH COMPRESSED GROOVES

BACKGROUND OF THE INVENTION

1. Field of the Invention

The present invention relates to an absorbent article including sanitary napkin, disposable diaper, urine absorbing pad and the like. More particularly, the present invention relates to an absorbent article which has a superior liquid absorption capacity and gives less discomfort that will be caused by contact between the bodily waste absorbed therein and the wearer's skin.

2. Description of the Related Art

Absorbent articles such as sanitary napkin are generally constructed to include a liquid-impermeable backsheet, an absorbent layer laid on it, and a liquid-permeable topsheet covering the absorbent layer. A menstrual blood as bodily waste passes through the topsheet and is retained by the absorbent layer.

When the absorbent article of this kind is attached to the wearer's body, it is required to prevent a liquid, which cannot be absorbed by the absorbent layer, from leaking outwardly beyond side edges of the absorbent article. In order to improve the wearing feel, it is also required to prevent the bodily waste once absorbed by the absorbent layer from oozing to the surface of the topsheet and coming into contact with the wearer's skin as much as possible In order to prevent the lateral leakage of the bodily waste beyond the side edges of the absorbent article, there has been developed an absorbent article having a nonwoven web disposed between the body fluid absorbent pad (absorbent layer) and the topsheet. In Japanese Unexamined Patent Publication No. H7-500759 (500759/1995), for example, there is disclosed an absorbent material having a nonwoven web between the liquid absorbent pad and the liquid-permeable topsheet.

In the absorbent material disclosed in the above-mentioned Patent Publication, the nonwoven web is provided with a screen pattern having high fiber density portions being oriented mainly in the longitudinal direction of the liquid absorbent pad. Therefore, a bodily waste having passed through the topsheet is diffused mainly in the longitudinal direction along the high density portions of the nonwoven web, thereby preventing the lateral leakage of the liquid.

As set forth above, the Patent Publication discloses an invention in which the nonwoven web is disposed between the topsheet and the liquid absorbent pad in order to diffuse the bodily waste mainly in the longitudinal direction of the liquid absorbent pad for absorption by the liquid absorbent pad. However, in this absorbent material having the nonwoven web mainly for liquid diffusion, there still remains a problem that when a pressure is applied from the wearer's skin, a liquid, which is not absorbed by the liquid absorbent pad but remains diffused in the nonwoven web, oozes to the surface of the topsheet and adheres to the wearer's skin again, giving discomfort due to wet feel to the wearer.

SUMMARY OF THE INVENTION

The present invention has been worked out in view of the shortcoming in the prior art set forth above. It is therefore an object of the present invention to provide an absorbent article having a good wearing feel, in which a liquid given to a top layer can rapidly migrate to an absorbent storage layer to prevent a liquid return to a surface of a top layer.

According to the invention, there is provided an absorbent article comprising:

a backsheet;
an absorbent storage layer;
a liquid guide layer; and
a top layer formed of at least one liquid-permeable layer, wherein the backsheet, the absorbent storage layer, the liquid guide layer, and the top layer are laminated one upon each other in the order named, wherein the absorbent storage layer, the liquid guide layer and the top layer satisfy the following relationships:

the liquid guide layer>the absorbent storage layer>the top layer with respect to a water absorbency due to capillary phenomenon;

the liquid guide layer>the absorbent storage layer>the top layer with respect to a retention ratio of a liquid dropped onto the top layer in an amount less than a maximum water absorption amount of the liquid guide layer; and the absorbent storage layer>the liquid guide layer>the top layer with respect to a retention ratio of a liquid dropped onto the top layer in an amount more than the maximum water absorption amount of the liquid guide layer.

In the absorbent article according to the present invention, since the water absorbency due to capillary phenomenon of the liquid guide layer is higher than that of the top layer, a liquid given to the top layer is rapidly absorbed by the liquid guide layer underlying it while being diffused therein. Therefore, the liquid is hardly stored in the top layer, reducing a wet feel on the surface of the top layer. On the other hand, since the water absorbency of the absorbent storage layer is lower than that of the liquid guide layer, a liquid, which is diffused and absorbed in the liquid guide layer and then introduced into the absorbent storage layer, is mainly guided along the thickness direction of the absorbent storage layer while being prevented from diffusing along the plane of the absorbent storage layer. Therefore, the liquid absorbed and retained by the absorbent storage layer does not excessively diffuse either longitudinally or laterally of the absorbent article, thereby preventing the possibility of lateral leakage.

In case where a small amount of liquid is given to the top layer, the liquid is immediately absorbed from the top layer to the liquid guide layer. In case where a relatively large amount of liquid is given to the top layer, on the other hand, the liquid is first absorbed by the liquid guide layer, and after the liquid guide layer is saturated with the liquid, the liquid is then absorbed by the absorbent storage layer having a higher water absorbency than the top layer. Thus, the absorbent article has a large liquid absorption capacity as a whole, and liquid return to the top layer is prevented.

As set forth above, since the liquid diffused and absorbed in the liquid guide layer is then absorbed by the absorbent storage layer while being prevented from diffusing along the plane of the absorbent storage layer, the liquid guide layer>the absorbent storage layer with respect to a diffusion area of a liquid dropped onto the top layer in an amount more than the maximum water absorption amount of the liquid guide layer.

For example, it is preferred that the top layer has a density of 0.01 to 0.1 g/cm$^3$, the liquid guide layer has a density of 0.05 to 0.2 g/cm$^3$, and the density of the liquid guide layer is larger than the density of the top layer. In this case, the water absorbency of the liquid guide layer can be made higher than that of the top layer, as set forth above, so that the liquid given to the top layer can be rapidly absorbed by the liquid guide layer while diffusing therein.

It is also preferred that the absorbent storage layer has a density of 0.05 to 0.2 g/cm$^3$, the liquid guide layer has a basis weight of 15 to 150 g/m$^2$, the absorbent storage layer has a basis weight of 150 to 850 g/m$^2$, and the basis weight of the absorbent storage layer is larger than the basis weight of the liquid guide layer. In this case, it is also preferred that the density of the liquid guide layer is larger than the density of the absorbent storage layer. With the basis weight of the absorbent storage layer being larger than the basis weight of the liquid guide layer, the liquid saturating the liquid guide layer can be easily absorbed by the absorbent storage layer in the thickness direction thereof, thereby increasing the liquid absorption capacity of the absorbent storage layer and also increasing the liquid retention capacity of the entire absorbent article.

Preferably, the liquid guide layer has a water absorption capacity of at least 18 times and a water retention capacity of at most 9 times. If the water absorption capacity is at least 18 times, the liquid once absorbed by the liquid guide layer hardly returns to the top layer. If the water retention capacity is at most 9 times, on the other hand, the liquid can be easily discharged from the liquid guide layer to the absorbent storage layer.

Preferably, the top layer and the liquid guide layer are joined to each other through joining means extending in a longitudinal direction of the absorbent article. In this case, the liquid given to the top layer can be absorbed by the liquid guide layer while being oriented in the longitudinal direction of the absorbent article, thereby suppressing the liquid diffusion laterally of the absorbent article.

Preferably, the absorbent storage layer is formed with compressed grooves, which are at opposite sides of a longitudinally extending centerline of the absorbent article and extend at least in the longitudinal direction, and the water absorbency due to capillary phenomenon of the compressed grooves is higher than that of the liquid guide layer. With such compressed grooves, a liquid tending to flow laterally is easily guided in the longitudinal direction along the compressed grooves, thereby preventing lateral diffusion of the liquid.

Preferably, the liquid guide layer has a length smaller than that of the absorbent storage layer and a width smaller than that of the absorbent storage layer, and longitudinally opposed front and rear edges and laterally opposed side edges of the liquid guide layer are inwardly spaced apart from longitudinally opposed front and rear edges and laterally opposed side edges of absorbent storage layer. In this case, the liquid discharged from the liquid guide layer to the absorbent storage layer upon saturation of the liquid guide layer can be centered at the central region of the absorbent storage layer, thereby preventing disadvantageous liquid diffusion in the absorbent storage layer toward the front and rear edges and the side edges thereof.

Preferably, an area of the liquid guide layer is smaller than those of the top layer and the absorbent storage layer, and the liquid guide layer is positioned between the compressed grooves. With the liquid guide layer positioned between the compressed grooves, the liquid absorbed from the liquid guide layer to the absorbent storage layer can be prevented from diffusing toward the front and rear edges and the side edges of the absorbent storage layer beyond the compressed grooves.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

Figure 1:
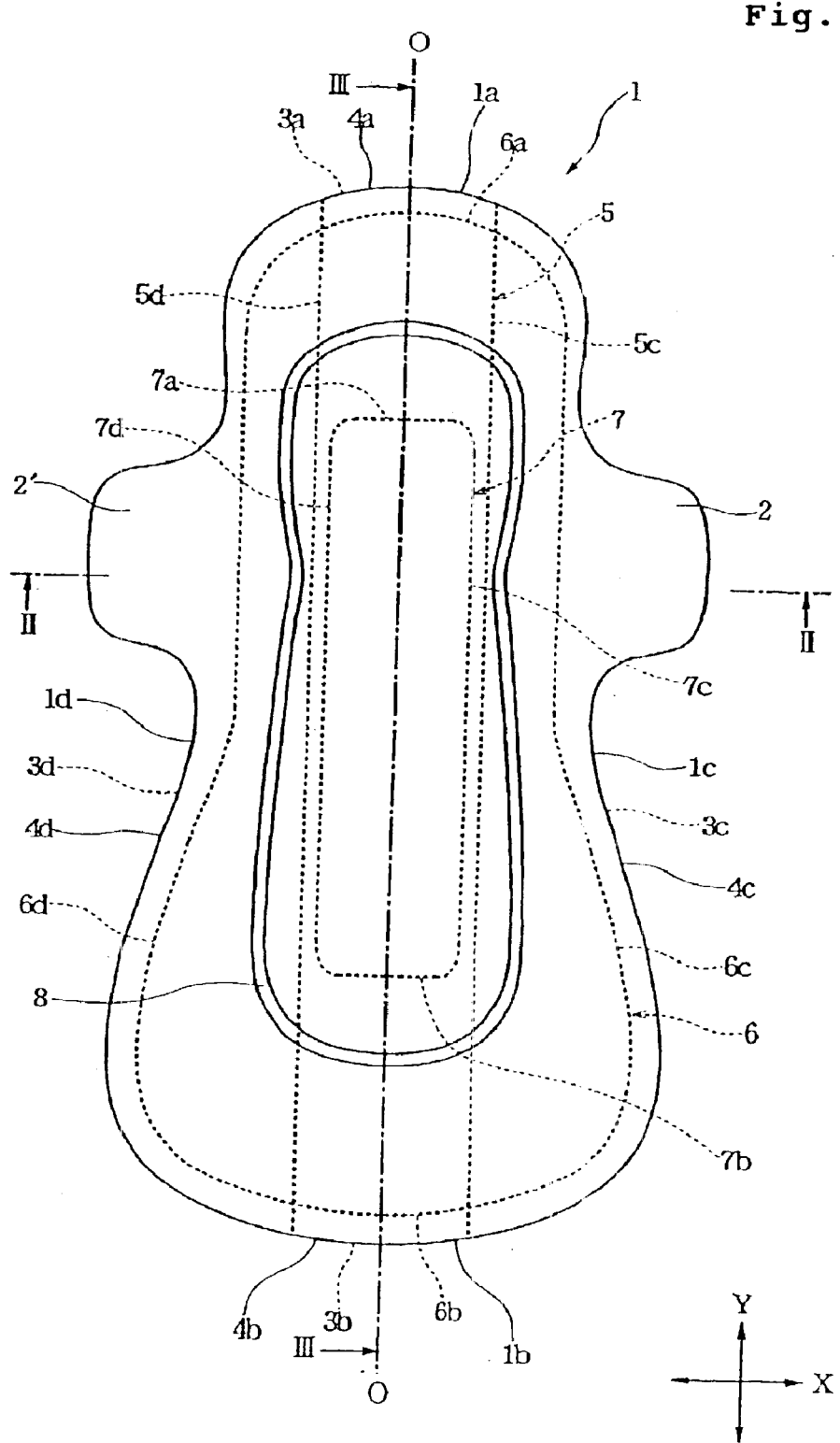
FIG. 1 is a top plan view showing a sanitary napkin as an absorbent article according to one embodiment of the present invention, as viewed from a wearer-facing side.
Figure 2:
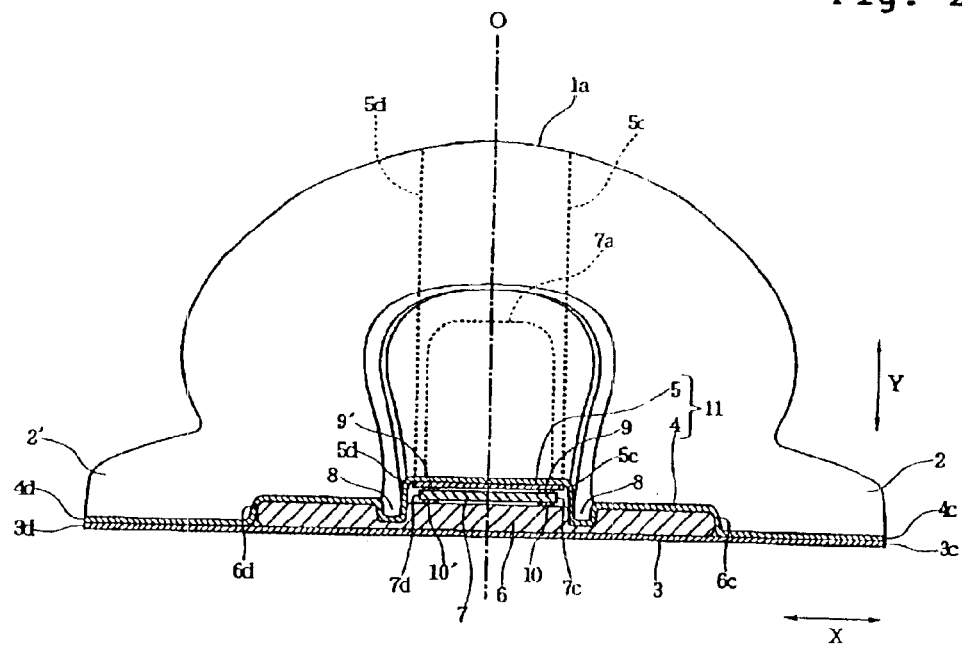
FIG. 2 is a cross sectional view taken along line II—II of FIG. 1.

FIG. 1 is a top plan view showing a sanitary napkin 1 as an absorbent article according to one embodiment of the present invention. FIG. 2 is a cross sectional view of the sanitary napkin 1 taken along line II—II of FIG. 1, and FIG. 3 is a longitudinal sectional view of the sanitary napkin 1 taken along line III—III (longitudinally extending centerline O—O) of FIG. 1.

Figure 3:
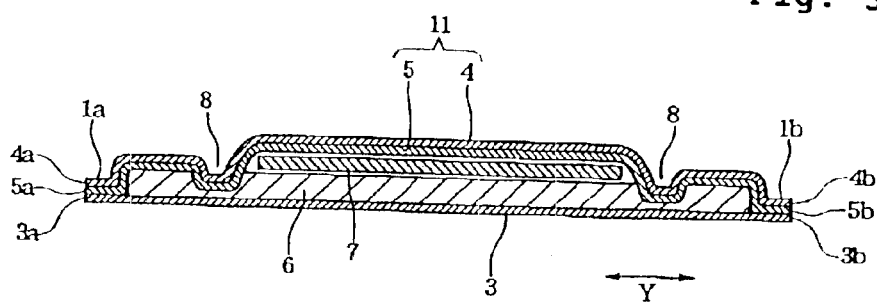
FIG. 3 is a longitudinal sectional view taken along line III—III of FIG. 1.

The sanitary napkin 1 shown in FIGS. 1 to 3 is to be worn by a female during menstruation while being attached to an inner side of a crotch portion of an undergarment.

As seen from the top plan view of FIG. 1, the sanitary napkin 1 has a generally arcuate front edge 1$a$ and a rear edge 1$b$ which is also arcuate but extended longer in the width direction (X-direction) than the front edge 1$a$. Right-hand and left-hand side edges 1$c$ and 1$d$ are curved. The distance between the right-hand side edge 1$c$ and the left-hand side edge 1$d$, i.e., the width (dimension in the X-direction) of the sanitary napkin 1 is larger in a rear portion on the side of the rear edge 1$b$, which is to be brought into contact mainly with the wearer's buttocks, than in a front portion on the side of the front edge 1$a$, which is to be brought into contact mainly with the wearer's crotch. The right-hand side edge 1$c$ and the left-hand side edge 1$d$ are protruded laterally (in the X-direction) outwardly in a position offset toward the front edge 1$a$ from a laterally extending centerline of the sanitary napkin 1, thereby forming wing portions 2 and 2'.

As shown in FIGS. 2 and 3, the sanitary napkin 1 comprises a liquid-impermeable backsheet 3 and first and second liquid-permeable topsheets 4 and 5. In the embodiment shown, a liquid-permeable top layer 11 is composed of the first and second topsheets 4 and 5. Between the backsheet 3 and the first and second topsheets 4 and 5, there is provided an absorbent storage layer (absorbent core) 6 capable of absorbing a liquid and retaining the absorbed liquid.

In addition, between the first and second topsheets 4 and 5 and the absorbent storage layer 6, there is provided a liquid guide layer (wicking layer) 7 capable of absorbing a liquid given to the first and second topsheets 4 and 5 and discharging the liquid into the absorbent storage layer 6.

The backsheet 3 has a front edge 3a, a rear edge 3b, a right-hand side edge 3c and a left-hand side edge 3d. The first topsheet 4 is in the uppermost position and forms a surface to be brought into contact with the wearer's skin. The first topsheet 4 has a front edge 4a, a rear edge 4b, a right-hand side edge 4c and a left-hand side edge 4d. The front edge 3a, the rear edge 3b, the right-hand side edge 3c and the left-hand side edge 3d of the backsheet 3 substantially coincide with the front edge 4a, the rear edge 4b, the right-hand side edge 4c and the left-hand side edge 4d of the first topsheet 4, respectively. The outline of the sanitary napkin 1 is defined by the respective edges of the backsheet 3 and the first topsheet 4.

The second topsheet 5 is positioned beneath the first topsheet 4 and has a width (dimension in the X-direction) smaller than that of the first topsheet 4. The length (dimension in the Y-direction) of the second topsheet 5 substantially coincides with that of the first topsheet 4, so that the second topsheet 5 extends over the entire length of the sanitary napkin 1 along the centerline O—O.

The first and second topsheets 4 and 5 may be formed of nonwoven fabrics having the same fiber density. Here, the second topsheet 5 may be formed of a single nonwoven fabric either unfolded or folded. Alternatively, the second topsheet 5 may be formed by stacking a plurality of nonwoven fabrics. It is also possible to vary the fiber density between the first and second topsheets 4 and 5. In this case, it is preferred that the second topsheet 5 has a higher fiber density than the first topsheet 4. If so, a liquid given to the first topsheet 4 can be introduced into the second topsheet 5, thereby preventing the occurrence of residual liquid on the first topsheet 4.

In the embodiment shown, the top layer is composed of the first and second topsheets 4 and 5. However, it is, of course, possible to form the top layer of a single topsheet.

As shown in FIGS. 2 and 3, the absorbent storage layer 6 is disposed on the backsheet 3. This absorbent storage layer 6 has a given thickness and has a periphery of a front edge 6a, a rear edge 6b, a right-hand side edge 6c and a left-hand side edge 6d, as shown in broken line in FIG. 1. The front and rear edges 6a and 6b of the absorbent storage layer 6 are similar in shape to the front and rear edges 1a and 1b of the sanitary napkin 1. The right-hand and left-hand side edges 6c and 6d of the absorbent storage layer 6 are similar in shape to the right-hand and left-hand side edges 1c and 1d of the sanitary napkin 1 except for the portions forming the wing portions 2 and 2'.

The front edge 6a, the rear edge 6b, the right-hand side edge 6c and the left-hand side edge 6d of the absorbent storage layer 6 are inwardly spaced apart form the front edge 1a, the rear edge 1b, the right-hand side edge 1c and the left-hand side edge 1d of the sanitary napkin 1 by 3 to 10 mm. In a region outside of the periphery (i.e., the front edge 6a, the rear edge 6b, the right-hand side edge 6c and the left-hand side edge 6d) of the absorbent storage layer 6, the backsheet 3 and the first topsheet 4 are bonded to each other either directly or through the second topsheet 5 using a hot-melt adhesive or the like.

As shown in FIGS. 1 and 2, the liquid guide layer 7 is disposed between the second topsheet 5 and the absorbent storage layer 6. The liquid guide layer 7 has a length (dimension in the Y-direction) smaller than that of the absorbent storage layer 6 and a width (dimension in the X-direction) smaller than that of the absorbent storage layer 6, so that the area of the liquid guide layer 7 is smaller than that of the absorbent storage layer 6. More specifically, as shown in FIG. 1, the front and rear edges 7a and 7b of the liquid guide layer 7 is positioned closer to the center of the sanitary napkin 1 than the front and rear edges 6a and 6b of the absorbent storage layer 6, and the right-hand and left-hand, side edges 7c and 7d of the liquid guide layer 7 is also positioned closer to the center of the sanitary napkin 1 than the right-hand and left-hand side edges 6c and 6d of the absorbent storage layer 6. Furthermore, the right-hand and left-hand side edges 7c and 7d of the liquid guide layer 7 is positioned closer to the centerline O—O than the right-hand and left-hand side edges 5c and 5d of the second topsheet 5.

As shown in FIG. 2, the lower surface (undergarment-facing surface) of the second topsheet 5 and the upper surface (wearer-facing surface) of the liquid guide layer 7 are facing each other and are bonded to each other with adhesives 9 and 9' being adopted as joining means. On the other hand, the lower surface of the liquid guide layer 7 and the upper surface of the absorbent storage layer 6 are facing each other and are bonded to each other with adhesives 10 and 10' being adopted as joining means.

The adhesives 9 and 9' are applied such that they are at opposite sides of the centerline O—O and extend in the longitudinal direction just inside the right-hand and left-hand side edges 7c and 7d of the liquid guide layer 7. Similarly, the adhesives 10 and 10' are applied such that they are at opposite sides of the centerline O—O and extend in the longitudinal direction just inside the right-hand and left-hand side edges 7c and 7d of the liquid guide layer 7.

Accordingly, a menstrual blood attracted by the liquid guide layer 7 through the top layer 11 composed of the first and second topsheets 4 and 5 hardly moves laterally beyond the right-hand and left-hand side edges 7c and 7d, on the surfaces of the liquid guide layer 7. Especially when the adhesives 9 and 9' and the adhesives 10 and 10' are mixed with a hydrophilic or water-repellent material, the liquid attracted by the liquid guide layer 7 through the top layer 11 can be effectively prevented from moving laterally beyond the adhesive layers, so that it can be absorbed by the liquid guide layer 7 while being diffused mainly along the longitudinal direction. Thus, the lateral leakage of the menstrual blood from the sanitary napkin 1 can be prevented.

Here, the joining means for joining the second topsheet 5 and the liquid guide layer 7 and the joining means for joining the liquid guide layer 7 and the absorbent storage layer 6 should not be limited to the adhesives. For example, heat-sealing may be performed along the longitudinal direction just inside the right-hand and left-hand side edges 7c and 7d of the liquid guide layer 7.

As shown in FIGS. 1, 2 and 3, the sanitary napkin 1 is formed with a compressed groove 8 surrounding the liquid guide layer 7. When the skin-contacting side of the sanitary napkin 1 is viewed from above, the compressed groove 8 is in an hourglass shape.

In the compressed groove 8, the first topsheet 4, the absorbent storage layer 6 and the backsheet 3 are heated under pressure, so that the absorbent storage layer 6 is compressed and recessed, and the first topsheet 4 is laid thereon in conformity with the recess. The embossing pattern for forming the compressed groove 8 may be either a pattern of continuous line or a pattern of intermittent embossments.

The width of the compressed groove 8 is preferably from 0.5 to 5 mm. If the width is less than 0.5 mm, the sanitary napkin 1 is liable to be cut at the compressed groove 8 during wear, deteriorating the durability of the sanitary napkin 1. If the width is more than 5 mm, the stiffness of the sanitary napkin 1 is excessively increased, resulting in causing a clearance between the wearer's body and the sanitary napkin 1 during wear. Therefore, a menstrual blood may possibly leak out of the sanitary napkin 1. More preferred range of the width of the compressed groove 8 is from 1.5 to 3 mm.

Next, liquid absorbency characteristics of the top layer 11 composed of the first and second topsheets 4 and 5, the absorbent storage layer 6, the liquid guide layer 7, and the compressed groove 8 will be described. Here, it should be noted that the fist and second topsheets 4 and 5 composing the top layer 11 in the shown embodiment are described as having the same density, basis weight and thickness.

(Water Absorbency by Klemm's Method)

The relationship of the first and second topsheets 4 and 5, the absorbent storage layer 6, and the liquid guide layer 7 will be described with respect to the water absorbency due to capillary phenomenon.

For measurement of the water absorbency by Klemm's method, the sheet materials of the first topsheet 4 and the second topsheet 5 are cut into separate samples having a length of 100 mm in MD (Machine direction) thereof and a width of 25 mm in CD (Cross direction) thereof. Likewise, the sheet materials of the absorbent storage layer 6 and the liquid guide layer 7 are cut into samples having a length of 100 mm in MD thereof and a width of 25 mm in CD thereof. It should be noted that the first and second topsheets 4 and 5, the absorbent storage layer 6, and the liquid guide layer 7 are used in the sanitary napkin 1 such that MDs of their sheet materials coincide with the longitudinal direction (Y-direction) of the sanitary napkin 1.

The samples thus prepared are suspended with MDs coinciding with the vertical direction, and then, the lower ends of the samples having a length of 15 mm are immersed in distilled water colored with a dye. Other conditions are in conformity to JIS-P8141. Water absorption heights after one minute are measured.

At this time, the relationship with respect to the water absorbency by Klemm's Method is required that the liquid guide layer 7>the absorbent storage layer 6>the first and second topsheets 4 and 5. With the water absorbency of the liquid guide layer 7 being set higher than that of the first and second topsheets 4 and 5, a menstrual liquid given to the first and second topsheets 4 and 5 can be absorbed by the liquid guide layer 7 below them, thereby preventing the occurrence of residual menstrual blood in the first and second topsheets 4 and 5. Therefore, the area and time of contact between the menstrual blood absorbed by the sanitary napkin 1 and the wearer's skin can be reduced, giving no discomfort to the wearer.

On the other hand, since the water absorbency of the absorbent storage layer 6 is set lower than that of the liquid guide layer 7, the liquid absorbed by and diffused in the liquid guide layer 7 is introduced into the absorbent storage layer 6 mainly along the thickness direction thereof while being prevented from diffusing along the plane of the absorbent storage layer 6. Therefore, the liquid absorbed and retained by the absorbent storage layer 6 does not excessively diffuse either in the longitudinal direction or in the width direction, thereby preventing the possibility of lateral leakage.

Here, in order to rapidly absorb a liquid given to the first and second topsheets 4 and 5 by the liquid guide layer 7, the water absorbency by Klemm's Method of the liquid guide layer 7 is preferably at least 40 mm, more preferably at least 50 mm.

Furthermore, when the water absorbency by Klemm's Method is measured for a sample, which is prepared by cutting the sheet material of the absorbent storage layer 6 to have a length of 100 mm in MD thereof and a width of 25 mm in CD thereof and then compressing the entire sample under the same condition as that for the compressed groove 8 of the sanitary napkin 1, the relationship with respect to the water absorbency by Klemm's Method is required that the compressed sample (the compressed groove 8)>the liquid guide layer 7>the absorbent storage layer 6>the first and second topsheets 4 and 5. With such relationship, when a menstrual blood absorbed in a region inside the compressed groove 8 reaches the compressed groove 8, such menstrual blood moves in the longitudinal direction along the compressed groove 8, thereby preventing the menstrual blood from moving beyond the compressed groove 8 and leaking outwardly, especially laterally.

(Liquid Retention Ratio)

At first, the maximum water absorption amount (water absorption saturation amount) of the liquid guide layer 7 is measured. A sample is prepared by cutting the sheet material of the liquid guide layer 7 employed for the sanitary napkin 1 into the same size as that of the liquid guide layer 7, and the weight of the sample is measured. Then, the sample is immersed in an artificial menstrual blood and taken out one minute later. After standing for one minute on a wire net, the weight of the sample is measured again. The maximum water absorption amount is obtained by subtracting the sample weight before absorption of the artificial menstrual blood from the sample weight after absorption of the artificial menstrual blood.

Here, the artificial menstrual blood contains 10% by weight of glycerin, 1% by weight of carboxymethyl cellulose and the balance being distilled water.

Next, the artificial menstrual blood is applied to the first topsheet 4 near the center of the liquid guide layer 7 of the sanitary napkin 1. At this time, the artificial menstrual blood is applied at a rate of 7 g/minute in an amount (e.g., 3 g) less than the maximum water absorption amount of the liquid guide layer 7. The artificial menstrual blood is also applied to the first topsheet 4 of another sanitary napkin 1 at a rate of 7 g/minute in an amount (e.g., 15 g) more than the maximum water absorption amount of the liquid guide layer 7. One minute after application of the artificial menstrual blood, the respective liquid retention ratios of the first and second topsheets 4 and 5, the liquid guide layer 7, and the absorbent storage layer 6 are measured for the respective sanitary napkins.

Here, the liquid retention ratio is obtained by $\{(\beta-\alpha)/\gamma\}\times 100(\%)$. In case of the liquid guide layer 7, the weight of the liquid guide layer 7 before application of the artificial menstrual blood is "$\alpha$", the weight of the liquid guide layer 7 after application of the artificial menstrual blood is "$\beta$", and the weight of the artificial menstrual blood dropped onto the first topsheet 4 is "$\gamma$" (in the above case, 3 g or 15 g). The first and second topsheets 4 and 5 are tested as a unit to obtain the liquid retention ratio of the top layer 11. In case of the absorbent storage layer 6, too, the liquid retention ratio is obtained similar to the case of the liquid guide layer 7.

In the sanitary napkin 1, the relationship of the layers with respect to the liquid retention ratio is such that:

the liquid guide layer 7>the absorbent storage layer 6>the top layer 11 (the first and second topsheets 4 and 5), when the artificial menstrual blood is applied in an amount (e.g., 3 g) less than maximum water absorption amount of the liquid guide layer 7; and the absorbent storage layer 6>the liquid guide layer 7>the top layer 11 (the first and second topsheets 4 and 5), when the artificial menstrual blood is applied in an amount (e.g., 15 g) more than maximum water absorption amount of the liquid guide layer 7.

With the relationship of the layers with respect to the liquid retention ratio being thus set, when a small amount of menstrual blood is given to the first topsheet 4 of the sanitary napkin 1, such a small amount of menstrual blood is rapidly absorbed by the liquid guide layer 7 from the first and second topsheets 4 and 5, and retained by the liquid guide layer 7. On the other hand, when a large amount of menstrual blood is given to the first topsheet 4 and the amount of the menstrual blood absorbed by the liquid guide layer 7 exceeds the maximum water absorption amount thereof, the menstrual blood is discharged from the liquid guide layer 7 to the absorbent storage layer 6 and stored in the absorbent storage layer 6.

Here, since the water absorbency of the absorbent storage layer 6 is higher than those of the first and second topsheets 4 and 5, the menstrual liquid introduced into the liquid guide layer 7 in an amount more than the maximum water absorption amount of the liquid guide layer 7 is hardly attracted by the first and second topsheets 4 and 5 from the liquid guide layer 7, but is absorbed and retained mainly by the absorbent storage layer 6. At this time, since the water absorbency of the absorbent storage layer 6 is lower than that of the liquid guide layer 7, as set forth above, the liquid migrating from the liquid guide layer 7 to the absorbent storage layer 6 is hardly diffused along the plane of the absorbent storage layer 6, but is absorbed by the absorbent storage layer 6 mainly along the thickness direction of the absorbent storage layer 6.

(Porosity of Top Layer 11)

The porosities of the first and second topsheets 4 and 5 after compression in a wet state are preferably at least 93%, more preferably at least 95%. If the porosities are less than 93%, a menstrual blood hardly passes through the first and second topsheets 4 and 5, so that the liquid guide layer 7 disposed beneath the second topsheet 5 cannot rapidly transport the menstrual blood to the absorbent storage layer 6.

For measurement of the porosities of the first and second topsheets 4 and 5 after compression in a wet state, the sheet materials of the first topsheet 4 and the second topsheet 5 are cut into samples having a size of 100 mm (in MD)×100 mm (in CD), and then, their basis weights are measured (the basis weight is represented by "v"). Then, 3 g of the artificial menstrual blood is dropped onto the sample put on a filter paper, and the sample is allowed to stand for one minute. Thereafter, a pressure of 3.43 kPa is applied to the sample for three minutes. One minute after removal of the pressure, the thickness of the sample is measured (the thickness is represented by "ξ"). The porosity after compression in a wet state is calculated by $[1-(v/\xi)]/(\text{fiber density})\times 100$. The term "fiber density" as used herein refers to a density of the sample in a dry state.

(Water Absorption Capacity and Water Retention Capacity of Liquid Guide Layer 7)

It is preferred that the liquid guide layer 7 has a water absorption capacity (water absorption magnification) of at least 18 times and a water retention capacity (water retention magnification) of at most 9 times, as measured by applying the artificial menstrual blood.

If the water absorption capacity of the liquid guide layer 7 is less than 18 times, the amount of liquid which can be temporarily retained by the liquid guide layer 7 becomes excessively small, so that the menstrual blood is liable to return to the first and second topsheets 4 and 5. If the water retention capacity of the liquid guide layer 7 is more than 9 times, on the other hand, the menstrual blood hardly moves to the absorbent storage layer 6. Therefore, a large amount of liquid is retained by the liquid guide layer 7 close to the wearer's skin, thereby providing a wet feel to the wearer.

For measurement of the water absorption capacity of the liquid guide layer 7, the sheet material of the liquid guide layer 7 is cut out to form a sample having the same size and thickness as those of the liquid guide layer 7 employed for the sanitary napkin 1, and then, the weight of the sample is measured (this weight is represented by "a"). Next, the sample is immersed in the artificial menstrual blood and taken out one minute later. After standing for one minute on a wire net, the weight of the sample is measured again (this weight is represented by "b"). The value calculated by (b/a)×100 represents the water absorption capacity.

For measurement of the water retention capacity of the liquid guide layer 7, the sample after standing for one minute on the wire net is subjected to an acceleration of 74.5 G for 90 seconds with a centrifugal machine. Thereafter, the weight of the sample is measured (this weight is represented by "c"). The value calculated by (c/a)×100 represents the water retention capacity.

(Liquid Diffusion Property)

The liquid diffusion property, the absorption speed and the liquid return ratio (wet back ratio) of the sanitary napkin 1, when the artificial menstrual blood is applied to the surface of the first topsheet 4 in an amount more than the maximum water absorption amount of the liquid guide layer 7, are determined as follows.

For measurement, 3 g of the artificial menstrual blood is applied to the first topsheet 4 of the sanitary napkin 1 in the period of 2 seconds, and 30 seconds later, 4 g of the artificial menstrual blood is applied thereto in the period of 2 seconds. One minute later, a filter paper is laid thereon and a pressure of 3.43 kPa is applied for 3 minutes. Immediately after removal of the pressure, 3 g of the artificial menstrual blood is applied thereto in the period of 2 seconds, and the time required for the artificial menstrual blood to penetrate into the sanitary napkin 1 from the surface of the first topsheet 4 and disappear from the surface of the first topsheet 4 is taken as the liquid absorption speed of the sanitary napkin 1.

Thereafter, 30 seconds later, 4 g of the artificial menstrual blood is dropped in the period of 2 seconds, and one minute later, a filter paper is laid thereon and a load of 3.43 kPa is applied for 3 minutes. In case where the weight of a liquid absorbed by the filter paper is "m" g, the liquid return ratio (wet back ratio) when a liquid is applied in an amount more than the maximum water absorption amount of the liquid guide layer 7 is represented by (m/14)×100(%). It should be noted that "14" in the formula refers to the total weight (G) of the applied liquid. Furthermore, after removal of the filter paper, the diffusion dimension of the menstrual blood is measured for the liquid guide layer 7 and the absorbent storage layer 6, respectively.

In the sanitary napkin 1, the liquid diffusion dimension (area) is preferably larger in the liquid guide layer 7 than in the absorbent storage layer 6.

On the other hand, the liquid absorption speed is preferably equal to or less than 30 seconds, more preferably equal to or less than 25 seconds. The liquid return ratio is preferably equal to or less than 68%, more preferably equal to or less than 60%. In case where the liquid absorption speed is equal to or less than 30 seconds and the liquid return ratio is equal to or less than 68%, a wet feel to the wearer's skin can be reduced when the sanitary napkin 1 is worn.

Next, materials of the respective layers constructing the sanitary napkin 1 will be described.

For example, the first and second topsheets 4 and 5 are formed of a through-air bonded nonwoven fabric, in which thermoplastic fibers forming a web are fusion-bonded with heated air. The fiber density of the through-air bonded nonwoven fabric is preferably 0.01 to 0.1 g/cm$^3$. If the fiber density is less than 0.01 g/cm$^3$, the number of fiber crossover points is small, deteriorating durability as the topsheet. If the fiber density is more than 0.1 g/cm$^3$, the liquid permeability is deteriorated, so that a menstrual blood hardly penetrates through it to the liquid guide layer 7. More preferred range of the density is 0.01 to 0.06 g/cm$^3$.

Fibers forming the through-air bonded nonwoven fabric are made of polyolefin macromolecule or polyester macromolecule. The fibers are preferably bicomponent synthetic fibers of sheath/core structure such as PET/PE or PP/PE, more preferably bicomponent synthetic fibers of eccentric (off-center) structure or hollow structure. In an alternative, the fibers may be, without limitation, bicomponent synthetic fibers of side-by-side structure such as PP/PP. These synthetic fibers are preferably treated to be hydrophilic by coating or mixing a hydrophilic agent. In an alternative, the through-air bonded nonwoven fabric may be made hydrophilic by mixing the hydrophobic synthetic fibers with hydrophilic fibers such as viscose rayon, acetate rayon or cotton fibers.

The diameter of the fibers forming the through-air bonded nonwoven fabric is preferably 10 to 50 $\mu$m, more preferably 15 to 35 $\mu$m. If the fiber diameter is less than 10 $\mu$m, when the fibers are accumulated into a fiber web, the distance between adjacent fibers becomes small, so that necessary porosity cannot be obtained. If the fiber diameter is more than 50 $\mu$m, on the other hand, the fiber stiffness is increased to give a foreign body sensation to the wearer.

The basis weight of the top layer 11 (total basis weight of the through-air bonded nonwoven fabrics forming the first and second topsheets 4 and 5) is preferably 15 to 120 g/m$^2$. If the basis weight is less than 15 g/m$^2$, since the distance between the wearer-facing surface of the top layer 11 and the liquid guide layer 7 is small, the menstrual blood retained by the liquid guide layer 7 is liable to return to the wearer-facing surface of the top layer 11 through the first and second topsheets 4 and 5, thereby causing the possibility of giving a wet feel due to the menstrual blood to the wearer. If the basis weight is more than 120 g/m$^2$, on the other hand, it takes a long time for the menstrual blood discharged onto the wearer-facing surface of the top layer 11 to reach the liquid guide layer 7, so that the liquid guide layer 7 cannot rapidly absorb the menstrual blood. More preferred range of the basis weight of the top layer 11 is 50 to 90 g/m$^2$.

It should be noted that the first and second topsheets 4 and 5 are not limited to such through-air bonded nonwoven fabric. For example, an open-cell foamed resin material may be employed.

Figure 4:
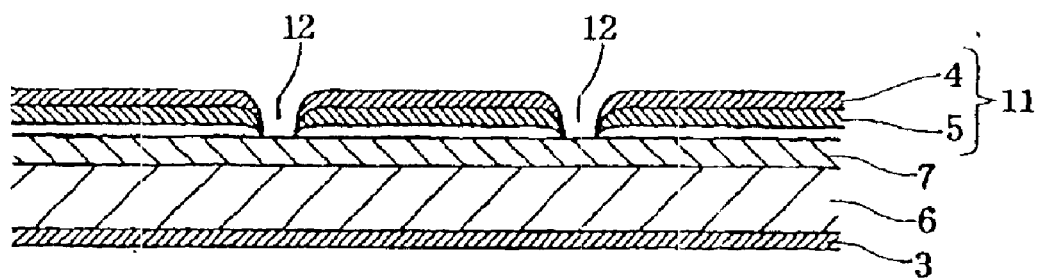
FIG. 4 is an enlarged view of a portion of FIG. 3.

As shown in a partial sectional view of FIG. 4, the top layer 11 composed of the first and second topsheets 4 and 5 may be formed with a large number of liquid passages 12 continuously passing through the first and second topsheets 4 and 5. These liquid passages 12 can be formed by piercing the laminate of the first and second topsheets 4 and 5 with needles. In this case, since the liquid guide layer 7 is exposed through the liquid passages 12, the menstrual blood given to the top layer 11 can be immediately absorbed by the liquid guide layer 7 through the liquid passages 12, thereby increasing the speed of absorbing the liquid by the liquid guide layer 7 through the top layer 11.

For example, the liquid guide layer 7 is formed of a spunlaced nonwoven fabric. The spunlaced nonwoven fabric means a nonwoven fabric in which accumulated fibers forming a web are entangled with jets of water to have high fiber density regions and low fiber density regions alternated both in MD and CD. In addition, by applying the water jets to the accumulated fiber web on a wire having a large number of apertures for entanglement, the nonwoven fabric can be formed with openings. In the case where the liquid guide layer 7 is formed of the spunlaced nonwoven fabric having the high and low density regions and the openings, the liquid is effectively permeated through the high density region and retained by the opening, providing superior water absorptive power and superior liquid diffusion property.

The fiber density of the spunlaced nonwoven fabric forming the liquid guide layer 7 is preferably 0.05 to 0.2 g/cm$^3$. If the fiber density is less than 0.05 g/cm$^3$, the force to attract the menstrual blood discharged on the first and second topsheets 4 and 5 to the liquid guide layer 7 is weakened. If the fiber density is more than 0.2 g/cm$^3$, on the other hand, the menstrual blood saturating the liquid guide layer 7 hardly moves to the absorbent storage layer 6.

Here, it is required that the fiber density of the liquid guide layer 7 is higher than the fiber density of the through-air bonded nonwoven fabric forming the top layer 11. By setting the difference in fiber density between the top layer 11 and the liquid guide layer 7, the liquid given to the top layer 11 can be rapidly absorbed by the liquid guide layer 7.

The basis weight of the liquid guide layer 7 is preferably 15 to 150 g/m$^2$. If the basis weight is less than 15 g/m$^2$, the maximum water absorption amount of the liquid guide layer 7 is too small. If the basis weight is more than 150 g/m$^2$, the water retention amount of the liquid guide layer 7 is excessively increased, so that the menstrual blood in the liquid guide layer 7 hardly moves to the absorbent storage layer 6.

The spunlaced nonwoven fabric mainly comprises hydrophilic regenerated cellulose fibers, preferably rayon fibers such as viscose rayon or acetate rayon. Alternatively, hydrophilic fibers such as cotton fibers, synthetic fibers made of polyolefin resin and treated with a hydrophilic agent to be hydrophilic, or synthetic fibers made of polyester resin and treated with a hydrophilic agent to be hydrophilic may be employed for the spunlaced nonwoven fabric. In order to increase the absorption speed of the liquid guide layer 7, moreover, the fibers forming the spunlaced nonwoven fabric are preferably modified cross-section fibers having a relatively large area/weight ratio, as exemplified by fibers having a cross-section of C or Y shape.

It should be noted that the liquid guide layer 7 is not limited to the spunlaced nonwoven fabric. For example, a laminate of tissue paper, air-laid pulp, fluff pulp, CTMP or the like may be employed for the liquid guide layer 7.

The absorbent storage layer 6 is composed of hydrophilic fibers, as exemplified by an aggregate of hydrophilic fibers such as fluff pulp, CTMP, or rayon fibers in which superabsorbent polymer is dispersed, or a sheet formed by wrapping hydrophilic fibers, superabsorbent polymer, and the like in air-laid pulp or tissue paper.

The fiber density of the absorbent storage layer 6 is preferably 0.05 to 0.2 g/cm$^3$. If the fiber density is less than 0.05 g/cm$^3$, it is difficult to absorb the menstrual blood from the liquid guide layer 7. If the fiber density is more than 0.2 g/cm$^3$, the menstrual blood absorbed by the absorbent storage layer 6 from the liquid guide layer 7 hardly moves toward the undergarment-facing surface of the absorbent storage layer 6, so that the absorbed menstrual blood excessively spreads in the wearer-facing surface of the absorbent storage layer 6. As set forth above, the sanitary napkin 1 requires that the water absorbency of the liquid guide layer 7 be higher than the water absorbency of the absorbent storage layer 6. To this end, it is preferred that the density of the liquid guide layer 7 is higher than that of the absorbent storage layer 6, or that the hydrophilicity of the fibers forming the liquid guide layer 7 is higher than that of the fibers forming the absorbent storage layer 6.

The basis weight of the absorbent storage layer 6 is preferably 150 to 850 g/m². If the basis weight is less than 150 g/m², the absorbent storage layer 6 is decreased in capability of absorbing and retaining water. If the basis weight is more than 850 g/m², on the other hand, the absorbent storage layer 6 is increased in thickness and stiffness, providing a foreign body sensation to the wearer. More preferably, the basis weight is 300 to 750 g/m².

The relationship between the basis weight of the liquid guide layer 7 and the basis weight of the absorbent storage layer 6 is preferably such that the basis weight of the absorbent storage layer 6 is at least twice as large as the basis weight of the liquid guide layer 7. By making the basis weight of the absorbent storage layer 6 larger than the basis weight of the liquid guide layer 7, when the menstrual blood is given to the absorbent storage layer 6 from the liquid guide layer 7, the menstrual blood retention capacity of the absorbent storage layer 6 can be increased.

When the sanitary napkin 1 thus constructed is used, the menstrual blood given to the top layer 11 can be rapidly absorbed by the liquid guide layer 7, thereby making the residual liquid on the top layer 11 very little. In addition, such menstrual blood is diffused and retained by the liquid guide layer 7, and when the menstrual blood saturates the liquid guide layer 7, it is immediately absorbed by the absorbent storage layer 6. At this time, the menstrual blood hardly diffuses along the plane of the absorbent storage layer6, but easily permeates in the thickness direction of the absorbent storage layer 6. Thus, the absorbent storage layer 6 can prevent liquid diffusion along its plane, thereby reducing the possibility of lateral leakage.

Especially in the foregoing embodiment, since the area of the liquid guide layer 7 is smaller than that of the absorbent storage layer 6, the menstrual blood diffused in the liquid guide layer 7 is absorbed by the absorbent storage layer 6 while being prevented from diffusing more. Therefore, the menstrual blood hardly permeates toward the front edge 6a, the rear edge 6b, the right-hand side edges 6c and the left-hand side edges 6d of the absorbent storage layer 6, thereby reducing the possibility of lateral leakage. Furthermore, since the periphery of the liquid guide layer 7 is surrounded by the compressed groove 8, the menstrual blood given to the absorbent storage layer 6 from the liquid guide layer 7 hardly permeates the outer region of the absorbent storage layer 6 beyond the compressed groove 8.

Hereinabove, the absorbent article of the present invention has been described embodied in a sanitary napkin. However, the absorbent article of the present invention is also applicable to other absorbent articles such as disposable diaper, urine absorbing pad, and the like.

EXAMPLES

As the respective layers of a sanitary napkin having the same structure as that of FIG. 1, various sheet materials were prepared. Tables 1 to 4 show the construction and properties of the respective layers. Table 1 shows the construction and properties of three kinds of topsheets; Table 2 shows the construction and properties of five kinds of liquid guide layers; Table 3 shows the construction and properties of two kinds of absorbent storage layers; and Table 4 shows the property of the compressed groove.

TABLE 1

| | Main component | Basic weight (g/m²) | Initial fiber density (g/cm³) | Fiber density after compression in wet (g/cm³) | Porosity after compression in wet (%) | Water absorbency by Klemm's Method After one minute (mm) |
|---|---|---|---|---|---|---|
| Topsheet-1 | PE/PP sheath/core through-air bonded nonwoven | 85 | 0.056 | 0.05 | 93.7 | 1 |
| Topsheet-2 | PE/PP sheath/core through-air bonded nonwoven | 85 | 0.02 | 0.03 | 96.8 | 1 |
| Topsheet-3 | PP spunbonded nonwoven | 20 | 0.066 | 0.07 | 92.6 | 1 |

TABLE 2

| | Main component | Basis weight (g/m²) | Water absorption capacity | Water retention capacity | Water absorbency by Klemm's Method After one minute (mm) |
|---|---|---|---|---|---|
| Liquid guide layer-1 | 100% rayon spunlaced nonwoven | 75 | 23.2 | 7.5 | 66 |
| Liquid guide layer-2 | Rayon/PET 50/50 spunlaced nonwoven | 75 | 19 | 8.3 | 58 |
| Liquid guide layer-3 | Tissue paper | 75 | 13.2 | 4.7 | 35 |
| Liquid guide layer-4 | Air-laid pulp | 75 | 11.8 | 6.6 | 54 |
| Liquid guide layer-5 | Fluff pulp | 75 | 20 | 9.1 | 22 |

TABLE 3

| | Main component | Basis weight (g/m²) | Thickness (mm) | Initial fiber density (g/cm³) | Water absorbency by Klemm's Method After one minute (mm) |
|---|---|---|---|---|---|
| Absorbent storage layer-1 | Pulp/SAP | 600/15 | 8 | 0.077 | 22 |
| Absorbent storage layer-2 | Pulp/SAP | 600/15 | 3 | 0.205 | 24 |

TABLE 4

| | Water absorbency by Klemm's Method After one minute (mm) |
|---|---|
| Compressed groove | 90 |

Examples

Preferred combinations of the topsheet, the liquid guide layer and the absorbent storage layer were selected from Tables 1 to 4 to prepare sanitary napkins of Examples 1, 2, 3, 4 and 5, as shown in Table 5.

was excessively diffused on the wearer-facing surface of the absorbent storage layer, so that it hardly moved toward the undergarment-facing surface in the absorbent storage layer. Therefore, the menstrual blood absorbed by the liquid guide layer to saturate the liquid guide layer could not be absorbed by the absorbent storage layer rapidly in the thickness direction thereof, thereby keeping the saturated state of the liquid guide layer. As a result, the absorption speed of the menstrual blood given to the top layer was low.

In Comparative Example 3, since the porosity of the top layer was excessively low, the artificial menstrual blood was easily left in the top layer and the absorption speed of the liquid from the top layer to the liquid guide layer was low. Therefore, the migration of the liquid from the liquid guide

TABLE 5

| | | | Ex. 1 | Ex. 2 | Ex. 3 | Ex. 4 | Ex. 5 |
|---|---|---|---|---|---|---|---|
| Constructions of Examples | | Topsheet<br>Liquid guide layer<br>Absorbent storage layer | Topsheet-2<br>Liquid guide layer-1<br>Absorbent storage layer-1 | Topsheet-2<br>Liquid guide layer-2<br>Absorbent storage layer-1 | Topsheet-1<br>Liquid guide layer-1<br>Absorbent storage layer-1 | Topsheet-2<br>Liquid guide layer-3<br>Absorbent storage layer-1 | Topsheet-2<br>Liquid guide layer-4<br>Absorbent storage layer-1 |
| Evaluation result | Liquid retention ratio (%) (at 15 g) | Topsheet | 5.4 | 5.5 | 5.5 | 7.5 | 6.8 |
| | | Liquid guide layer | 8.7 | 8.3 | 8.8 | 11 | 15 |
| | | Absorbent storage layer | 85.9 | 86.2 | 85.7 | 81.5 | 78.2 |
| | Evaluation of absorbency | Diffusion dimension (mm) in length | 60 | 61 | 62 | 68 | 65 |
| | | Diffusion dimension (mm) in width | 28 | 27 | 31 | 33 | 32 |
| | | Liquid return ratio (%) | 55 | 54 | 56 | 68 | 64 |
| | | Absorption speed (second) | 9.4 | 9.8 | 12.2 | 25 | 24 |

Comparative Examples

Other combinations of the topsheet, the liquid guide layer and the absorbent storage layer were selected to prepare sanitary napkins of Comparative Examples 1, 2, 3, and 4, as shown in Table 6.

layer to the absorbent storage layer was also slow, so that the liquid was diffused on the wearer-facing surface of the absorbent storage layer.

In Comparative Example 4, since the water retention capacity (water retention magnification) of the liquid guide layer was high, the artificial menstrual blood hardly

TABLE 6

| | | | Com. Ex. 1 | Com. Ex. 2 | Com. Ex. 3 | Com. Ex. 4 |
|---|---|---|---|---|---|---|
| Constructions of Comparative Examples | | Topsheet<br>Liquid guide layer<br>Absorbent storage layer | Topsheet-1<br>—<br>Absorbent storage layer-1 | Topsheet-2<br>Liquid guide layer-1<br>Absorbent storage layer-2 | Topsheet-3<br>Liquid guide layer-1<br>Absorbent storage layer-1 | Topsheet-2<br>Liquid guide layer-5<br>Absorbent storage layer-1 |
| Evaluation result | Liquid retention ratio (%) (at 15 g) | Topsheet | 7.7 | 8 | 12 | 6.9 |
| | | Liquid guide layer | | 9 | 10 | 14.8 |
| | | Absorbent storage layer | 92.3 | 83 | 78 | 78.3 |
| | Evaluation of absorbency | Diffusion dimension (mm) in length | 70 | 68 | 88 | 67 |
| | | Diffusion dimension (mm) in width | 40 | 46 | 56 | 51 |
| | | Liquid return ratio (%) | 69 | 57 | 75 | 74 |
| | | Absorption speed (second) | 41.8 | 35 | 42 | 48 |

<Evaluation>

In Comparative Example 1, since there was no liquid guide layer, the absorption speed of the artificial menstrual blood given to the top layer was low.

In Comparative Example 2, since the fiber density of the absorbent storage layer was high, the menstrual blood given from the liquid guide layer to the absorbent storage layer migrated from the liquid guide layer to the absorbent storage layer, so that the absorption speed was low as a whole.

In Examples 1 to 5, on the other hand, the liquid diffusion area in the absorbent storage layer was small, the liquid absorption speed was equal to or less than 25 seconds, and the liquid return ratio was equal to or less than 68%.

Therefore, when the sanitary napkins of Examples 1 to 5 are worn, a wet feel to the wearer's skin can be reduced.

As has been described above, in the absorbent article of the present invention, a body fluid discharged onto the top layer can be guided through the liquid guide layer to the absorbent storage layer, thereby eliminating return of the body fluid thus absorbed and retained. In addition, the body fluid absorbed by the absorbent article hardly diffuses along a plane of the absorbent article, thereby reducing a wet area due to the absorbed and retained body fluid. Accordingly, the absorbed body fluid hardly gives a wet feel to the wearer.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. An absorbent article comprising:
    a backsheet;
    an absorbent storage layer formed with compressed grooves, which are at opposite sides of a longitudinally extending centerline of the absorbent article and extend at least in the longitudinal direction;
    a liquid guide layer; and
    a top layer formed of at least one liquid-permeable layer, wherein the backsheet, the absorbent storage layer, the liquid guide layer, and the top layer are laminated one upon each other in the order named, wherein
    the absorbent storage layer, the liquid guide layer and the top layer satisfy the following relationships:
    the liquid guide layer is greater that the absorbent storage layer which is greater than the top layer with respect to a water absorbency due to capillary phenomenon;
    the liquid guide layer is greater than the absorbent storage layer which is greater than the top layer with respect to a retention ratio of a liquid dropped onto the top layer in an amount less than a maximum water absorption amount of the liquid guide layer; and
    the absorbent storage layer is greater than the liquid guide layer which is greater than the top layer with respect to a retention ratio of a liquid dropped onto the top layer in an amount more than the maximum water absorption amount of the liquid guide layer;
    wherein the water absorbency due to capillary phenomenon of the compressed grooves is higher than that of the liquid guide layer.

2. The absorbent article as set forth in claim 1, wherein the liquid guide layer is greater than the absorbent storage layer with respect to a diffusion area of a liquid dropped onto the top layer in an amount more than the maximum water absorption amount of the liquid guide layer.

3. The absorbent article as set forth in claim 1, wherein the top layer has a density of 0.01 to 0.1 g/cm$^3$, the liquid guide layer has a density of 0.05 to 0.2 g/cm$^3$, and the density of the liquid guide layer is larger than the density of the top layer.

4. The absorbent article as set forth in claim 3, wherein the absorbent storage layer has a density of 0.05 to 0.2 g/cm$^3$, the liquid guide layer has a basis weight of 15 to 150 g/m$^2$, the absorbent storage layer has a basis weight of 150 to 850 g/m$^2$, and the basis weight of the absorbent storage layer is larger than the basis weight of the liquid guide layer.

5. The absorbent article as set forth in claim 1, wherein the top layer and the liquid guide layer are joined to each other through joining means extending in a longitudinal direction of the absorbent article.

6. The absorbent article as set forth in claim 1, wherein the liquid guide layer has a length smaller than that of the absorbent storage layer and a width smaller than that of the absorbent storage layer, and longitudinally opposed front and rear edges and laterally opposed side edges of the liquid guide layer are inwardly spaced apart from longitudinally opposed front and rear edges and laterally opposed side edges of absorbent storage layer.

7. The absorbent article as set forth in claim 1, wherein an area of the liquid guide layer is smaller than those of the top layer and the absorbent storage layer, and the liquid guide layer is positioned between the compressed grooves.

* * * * *